United States Patent [19]

Weis et al.

[11] 4,258,194
[45] Mar. 24, 1981

[54] PROCESS FOR PRODUCING 2,3,5-TRICHLOROPYRIDINE

[75] Inventors: Claus D. Weis, Pfeffingen; Peter Sutter, Muttenz, both of Switzerland

[73] Assignee: Ciba-Geigy Corporation, Ardsley, N.Y.

[21] Appl. No.: 74,216

[22] Filed: Sep. 10, 1979

[51] Int. Cl.³ .......................................... C07D 213/02
[52] U.S. Cl. .................................. 546/345; 260/924; 260/987
[58] Field of Search ........................................ 546/345

[56] References Cited

U.S. PATENT DOCUMENTS 4,111,938  9/1978  Redemann .......................... 546/345

*Primary Examiner*—Alan L. Rotman
*Attorney, Agent, or Firm*—Karl F. Jorda

[57] ABSTRACT

A novel process for producing 2,3,5-trichloropyridine is described. In this process, 2,3,4,5-tetrachloropyridine is reacted, in an alkanephosphonic acid dialkyl ester (dialkyl alkane phosphonate) having 1 to 4 carbon atoms in each of the alkyl groups or in a phosphoric acid trialkyl ester (trialkyl phosphate) having 1 to 4 carbon atoms in each of the alkyl groups as the solvent, at 60° to 120° C., in the presence of 1.4 to 2.8 mols, per mol of 2,3,4,5-tetrachloropyridine, of an ammonium salt of an inorganic or organic acid, with 1.2 to 1.6 gram atoms of zinc per mol of 2,3,4,5-tetrachloropyridine, the 2,3,4,5-tetrachloropyridine being selectively dechlorinated in the 4-position.

2,3,5-Trichloropyridine is a valuable intermediate for producing herbicidally effective α-[4-(3',5'-dichloropyrid-2-yloxy)-phenoxy-]-alkanecarboxylic acids and derivatives thereof.

There are also described novel ammonium salts of methanephosphonic acid monomethyl ester, in the presence of which salts the selective dechlorination of 2,3,4,5-tetrachloropyridine in the 4-position is advantageously performed.

11 Claims, No Drawings

PROCESS FOR PRODUCING 2,3,5-TRICHLOROPYRIDINE

The present invention relates to a process for producing 2,3,5-trichloropyridine.

2,3,5-Trichloropyridine is a valuable intermediate for producing herbicidally effective α-[4-(3',5'-dichloropyrid-2-yloxy)-phenoxy]-alkanecarboxylic acids and derivatives thereof. The production and use of such α-[4-(3',5'-dichloropyrid-2-yloxy)-phenoxy]-alkanecarboxylic acids and derivatives thereof are described for example in the U.S. Pat. No. 4,092,151.

The method of producing 2,3,5-trichloropyridine by reaction of N-methyl-3,5-dichloro-2-pyridone with phosgene is known (Ann. Chem. 486, 71, 78 (1931)). The N-methyl-3,5-dichloro-2-pyridone required as starting material is obtained by chlorination of N-methyl-2-pyridone (J. pr. Chem. 93, 371 (1916)), which for its part can be produced by electrolytic oxidation of N-methylpyridinium sulfate (J. pr. Chem. 93, 363 (1916)), or by reaction of 2-aminopyridine with potassium nitrite in an acid medium and methylation of the formed 2-pyridone with dimethyl sulfate (Ann. Chem. 489, 109, 110 (1931)).

Furthermore, from the U.S. Pat. No. 4,111,938 is known a method of producing 2,3,5-trichloropyridine by dechlorination of pentachloropyridine or 2,3,5,6-tetrachloropyridine with zinc dust in an alkaline medium, at a pH value of above 11, in the presence of water and of a solvent immiscible with water.

It has now been found that 2,3,5-trichloropyridine can be produced in good yield and degree of purity by reacting 2,3,4,5-tetrachloropyridine, in an alkanephosphonic acid dialkyl ester (dialkyl alkane phosphonate) having 1 to 4 carbon atoms in each of the alkyl groups or in a phosphoric acid trialkyl ester (trialkyl phosphate) having 1 to 4 carbon atoms in each of the alkyl groups as the solvent, at 60°–120° C., in the presence of 1.4 to 2.8 mols, per mol of 2,3,4,5-tetrachloropyridine, of an ammonium salt of an inorganic or organic acid, with 1.2 to 1.6 gram atoms of zinc per mol of 2,3,4,5-tetrachloropyridine.

Suitable alkanephosphonic acid dialkyl esters which can be used as solvent according to the invention are for example: the dimethyl, diethyl, di-n-propyl, diisopropyl, di-n-butyl, di-sec-butyl, diisobutyl and di-tert-butyl esters of methane-, ethane-, 1-methylethane-, 1,1-dimethylethane-, propane-, 1-methylpropane-, 2-methylpropane- and butanephosphonic acid. Preferred alkanephosphonic acid dialkyl esters are methanephosphonic acid dimethyl ester and ethanephosphonic acid diethyl ester.

Suitable phosphoric acid trialkyl esters which can be used according to the invention as solvent are for example: phosphoric acid trimethyl ester, phosphoric acid triethyl ester, phosphoric acid tri-n-propyl ester, phosphoric acid triisopropyl ester and phosphoric acid tributyl ester. Preferred phosphoric acid trailkyl esters are phosphoric acid trimethyl ester and phosphoric acid triethyl ester.

Within the temperature range of 60°–120° C., in which the process according to the invention can be performed, temperatures of 85°–90° C. are preferred.

The ammonium salts usable according to the invention contain as cation the ammonium ion, or the derivatives thereof derived by partial or complete replacement of the hydrogen atoms by alkyl and/or phenyl groups, whereby the phenyl groups can be substituted by simple substituents such as alkyl, alkoxy or halogen. The ammonium salts usable according to the invention contain as anion the radical of an inorganic or organic acid capable of forming ammonium salts.

Ammonium salts which can be advantageously used correspond to the formula

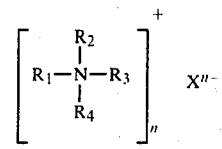

in which $R_1$, $R_2$, $R_3$ and $R_4$ can be identical or different and are each hydrogen, alkyl having 1 to 4 carbon atoms, or phenyl which can be substituted by halogen, by alkyl groups having 1 to 4 carbon atoms or by alkoxy groups having 1 to 4 carbon atoms, X is an anion from the group: chloride, bromide, sulfate, hydrogen sulfate, phoshpate, hydrogen phosphate, dihydrogen phosphate, carbonate, hydrogen carbonate, acetate, propionate, butyrate, isobutyrate, oxalate, benzoate, alkanephosphonate having 1 to 4 carbon atoms in the alkyl group and alkane- or benzenesulfonate having 1 to 4 carbon atoms in the alkyl group, and n is 1 to 3 and corresponds to the number of negative charges of the respective anion X.

To be mentioned as further ammonium salts that can be advantageously used are the ammonium salts of the methanephosphonic acid monomethyl ester of the formula

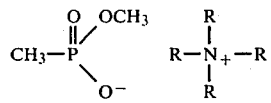

in which R is hydrogen or methyl. These ammonium salts are novel compounds which can be obtained in a simple manner by heating ammonium chloride or tetramethylammonium chloride in methanephosphonic acid dimethyl ester (dimethylmethane phosphonate) to 150° C., with methyl chloride being split off. The reaction is advantageously performed in excess methanephosphonic acid dimethyl ester as solvent. After the reaction is completed, the excess methanephosphonic acid dimethyl ester is distilled off in vacuo, and the ammonium salt, optionally after digestion in a suitable solvent, for example acetone, methyl ethyl ketone or ether, is obtained in crystalline form.

Preferred ammonium salts are ammonium chloride, ammonium sulfate, ammonium carbonate, the ammonium salt of methanephosphonic acid monomethyl ester and the tetramethylammonium salt of methanephosphonic acid monomethyl ester. The ammonium salt of methanephosphonic acid monomethyl ester and the tetramethylammonium salt of methanephosphonic acid monomethyl ester are particularly preferred.

With the use of methanephosphonic acid dialkyl ester as solvent, the aforementioned ammonium salts are used preferably in an amount of 1.6 mols per mol of 2,3,4,5-tetrachloropyridine. When ethanephosphonic acid dialkyl ester or phosphoric acid trialkyl ester is used as solvent, there are preferably used 2.6–2.7 mols of ammonium salt per mol of 2,3,4,5-tetrachloropyridine.

3

The zinc to be used according to the invention is used in the form of zinc chips or preferably in the form of zinc dust. There are preferably used 1.20–1.30 gram atoms of zinc per mol of 2,3,4,5-tetrachloropyridine.

It is possible using the process according to the invention to produce 2,3,5-trichloropyridine, by selective dechlorination of 2,3,4,5-tetrachloropyridine, in good yield and with a high degree of purity. 2,3,4,5-Tetrachloropyridine is a readily accessible starting material, which can be obtained for example using a process described in the U.S. Pat. No. 3,555,032 by chlorination of the hydrochloride of 2-chloropyridine, which for its part can be produced by chlorination of pyridine (see U.S. Pat. Nos. 2,820,791 and 2,839,534).

The process according to the invention is further illustrated by the following Examples.

EXAMPLE 1

A suspension of 11.0 g (0.05 mol) of 2,3,4,5-tetrachloropyridine and 4.4 g (0.065 gram atom) of zinc dust (96.6%) in 90 ml of methanephosphonic acid dimethyl ester is heated with stirring to 85° C. There is then added dropwise within 35 minutes a solution of 13.7 g (0.075 mol) of the tetramethylammonium salt of methanephosphonic acid monomethyl ester in 31 ml of water. After completed addition of the tetramethylammonium salt, the temperature of the mixture is held for one further hour at 85° C. The undissolved metal is subsequently filtered off, and the filtrate is poured into a mixture of 500 ml of ice water and 12.5 ml of concentrated hydrochloric acid. The resulting white crystal suspension is stirred for 2 hours and then filtered. The filter residue is washed with 100 ml of water and dried over potassium hydroxide to thus obtain 7.3 g (78.9% of theory) of 2,3,5-trichloropyridine which has a melting point of 46.5° to 47.5° C. and which, according to gas-chromatographical analysis, contains 96.4% of 2,3,5-trichloropyridine, 0.6% of 2,3,4,5-tetrachloropyridine and 1.7% of unknown products.

The employed tetramethylammonium salt of methanephosphonic acid methyl ester can be produced as follows:

In a 1-liter flask with a mounted reflux condenser, 540 g (4 mols) of methanephosphonic acid dimethyl ester and 219 g (2 mols) of tetramethylammonium chloride are heated with stirring to 130° C., in the course of which the reaction commences with the evolution of methyl chloride. The temperature is then raised within 3 hours to 150° C., and the reaction mixture is heated for a further hour at 160° C. The clear colourless solution is subsequently evaporated to dryness at 12 Torr. To the white crystalline residue is added 400 ml of acetone, and the whole is stirred for 30 minutes at 0° C. and then filtered. The product is washed on the filter with 500 ml of ether, and afterwards dried at 60° C. and 12 Torr over solid potassium hydroxide to yield 312 g (85% of theory) of tetramethylammonium salt of methanephosphonic acid monomethyl ester, m.p. 172°–177° C. (decomposition), in the form of white crystals.

EXAMPLE 2

By the method described in Example 1, 11.0 g (0.05 mol) of 2,3,4,5-tetrachloropyridine, 4.4 g (0.065 gram atom) of zinc dust (96%) and 4.0 g (0.075 mol) of ammonium chloride are reacted to yield 7.1 g (78% of theory) of 2,3,5-trichloropyridine, m.p. 36°–40° C., which contains, according to gas-chromatographical analysis, 79.2% of 2,3,5-trichloropyridine, 11.8% of 2,3,4,5-tetrachloropyridine and 6.6% of unknown products.

EXAMPLE 3

By the method described in Example 1, 11.0 g (0.05 mol) of 2,3,4,5-tetrachloropyridine, 4.4 g (0.065 gram atom) of zinc dust (96.5%) and 24.7 g (0.135 mol) of the tetramethylammonium salt of methanephosphonic acid monomethyl ester in 90 ml of trimethyl phosphate are reacted to obtain 7.1 g (78% of theory) of 2,3,5-trichloropyridine, m.p. 47°–47.5° C., which contains, according to gas-chromatographical analysis, 97.6% of 2,3,5-trichloropyridine, 0.4% of 2,3,4,5-tetrachloropyridine and 1.4% of unknown products.

EXAMPLE 4

By the method described in Example 1, 11.0 g (0.05 mol) of 2,3,4,5-tetrachloropyridine, 4.4 g (0.065 gram atom) of zinc dust (96%) and 9.5 g (0.075 mol) of the ammonium salt of methanephosphonic acid monomethyl ester are reacted to obtain 7.0 g (76% of theory) of 2,3,5-trichloropyridine, m.p. 37°–40° C., which contains, according to gas-chromatographical analysis, 78.8% of 2,3,5-trichloropyridine, 2.5% of 2,3,4,5-tetrachloropyridine and 0.61% of unknown products.

The ammonium salt of methanephosphonic acid monomethyl ester can be produced as follows:

In a 1-liter round-bottomed flask with mounted reflux condenser, 540 g (4 mols) of methanephosphonic acid dimethyl ester and 107 g (2 mols) of ammonium chloride are heated, with stirring, to 110° C., the reaction commencing with the evolution of methyl chloride. The temperature is then raised within 20 minutes to 138° C., and subsequently within a further 20 minutes to 151° C. The clear colourless solution is afterwards evaporated at 12 Torr to dryness to obtain, as residue, a yellow oil which, after the addition of 500 ml of acetone, is stirred for 24 hours, with crystallisation occurring. The crystal suspension is cooled to 0° C., filtered, and subsequently washed on the filter, with exclusion of moisture, with 150 ml of ether. After drying at 50° C. at 12 Torr, there is obtained 118.6 g (46.7% of theory) of the ammonium salt of methanephosphonic acid monomethyl ester, m.p. 96°–103° C., in the form of highly hydroscopic crystals, which soon deliquesce on standing in air.

What is claimed is:

1. A process for producing 2,3,5-trichloropyridine, which process comprises reacting 2,3,4,5-tetrachloropyridine, in an alkanephosphonic acid dialkyl ester having 1 to 4 carbon atoms in each of the alkyl groups or in a phosphoric acid trialkyl ester having 1 to 4 carbon atoms in each of the alkyl groups as the solvent, at 60°–120° C., in the presence of 1.4 to 2.8 mols, per mol of 2,3,4,5-tetrachloropyridine, of an ammonium salt of an inorganic or organic acid, with 1.2 to 1.6 gram atoms of zinc per mol of 2,3,4,5-tetrachloropyridine.

2. A process according to claim 1, wherein an alkanephosphonic acid dialkyl ester is used which is methanephosphonic acid dimethyl ester or ethanephosphonic acid diethyl ester.

3. A process according to claim 1, wherein a phosphoric acid trialkyl ester is used which is phosphoric acid trimethyl ester or phosphoric acid triethyl ester.

4. A process according to claim 1, wherein the reaction is performed at 85°–90° C.

5. A process according to claim 1, wherein there is used an ammonium salt of the formula

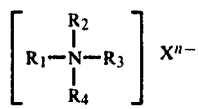

in which $R_1$, $R_2$, $R_3$ and $R_4$ can be identical or different and are each hydrogen, alkyl having 1 to 4 carbon atoms, or phenyl which can be substituted by halogen, by alkyl groups having 1 to 4 carbon atoms, or by alkoxy groups having 1 to 4 carbon atoms, X is an anion from the group consisting of chloride, bromide, sulfate, hydrogen sulfate, phosphate, hydrogen phosphate, dihydrogen phosphate, carbonate, hydrogen carbonate, acetate, propionate, butyrate, isobutyrate, oxalate, benzoate, alkanephosphonate having 1 to 4 carbon atoms in the alkyl group and alkane- or benzenesulfonate having 1 to 4 carbon atoms in the alkyl group, and n is 1 to 3 and corresponds to the number of negative charges of the respective anion X.

6. A process according to claim 1, wherein there is used an ammonium salt of the methanesulfunic acid monomethyl ester of the formula

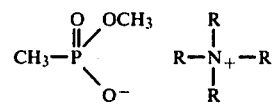

in which R is hydrogen or methyl.

7. A process according to claim 1, wherein the ammonium salt used is ammonium chloride, ammonium sulfate, ammonium carbonate, the ammonium salt of methanephosphonic acid monomethyl ester or the tetramethylammonium salt of methanephosphonic acid monomethyl ester.

8. A process according to claim 7, wherein the ammonium salt used is the ammonium salt of methanephosphonic acid monomethyl ester or the tetramethylammonium salt of methanephosphonic acid monomethyl ester.

9. A process according to claim 1, wherein, with the use of methanephosphonic acid dialkyl ester as solvent, there are used 1.6 mols of ammonium salt per mol of 2,3,4,5-tetrachloropyridine.

10. A process according to claim 1, wherein, with the use of ethanephosphonic acid dialkyl ester or trialkyl phosphate as solvent, there are used 2.6 to 2.7 mols of ammonium salt per mol of 2,3,4,5-tetrachloropyridine.

11. A process according to claim 1, wherein 1.2–1.3 gram atoms of zinc are used per mol of 2,3,4,5-tetrachloropyridine.

* * * * *